United States Patent [19]
Kostich

[11] Patent Number: 5,433,220
[45] Date of Patent: Jul. 18, 1995

[54] PATIENT GRIP POSITIONER

[76] Inventor: Jeffrey V. Kostich, 8433 Scenic Ridge NW., Clinton, Ohio 44216

[21] Appl. No.: 251,477

[22] Filed: May 31, 1994

[51] Int. Cl.⁶ .......................... A61G 15/00; A61F 5/00
[52] U.S. Cl. ........................................ 128/845; 602/32
[58] Field of Search ............... 128/845, 846; 482/140, 482/142, 145; 602/32, 33, 35, 39, 40; 606/237

[56] References Cited

U.S. PATENT DOCUMENTS

| | | | |
|---|---|---|---|
| 3,491,385 | 1/1970 | Werner | 128/845 |
| 4,337,942 | 7/1982 | Sidlinger | 482/145 |
| 4,679,788 | 7/1987 | Adler | 482/140 |
| 4,863,158 | 9/1989 | Tassone | 482/140 |
| 5,120,052 | 6/1992 | Evans | 482/140 |
| 5,195,938 | 3/1993 | Robertson | 482/140 |
| 5,306,220 | 4/1994 | Kearney | 482/145 |

OTHER PUBLICATIONS

"Smithers Unveils Re-Positioning Technology for the 21st Century", p. 18, published by Smithers Medical Products Inc. (22 pages, undated).

*Primary Examiner*—Michael A. Brown
*Attorney, Agent, or Firm*—Oldham, Oldham and Wilson Co.

[57] ABSTRACT

Device for positioning of patient in an arms-over-head position. This device comprises a horizontal base which is placed on a horizontal supporting surface such as a floor or patient treatment table, a head positioning member affixed to the base near one end thereof, an upright handlebar supporting member which is secured to the base near another end thereof and extends upwardly from the base, and a handlebar which is adjustably mounted in or on the handlebar support member so that the hand grips on the handlebar may be positioned either closer to or farther from the head positioning member, in accordance with the height and arm length of the patient. This device is useful in medical procedures in which a patient should be precisely and reproducibly positioned in an arms-over-head position.

7 Claims, 1 Drawing Sheet

PATIENT GRIP POSITIONER

TECHNICAL FIELD

This invention relates to a device for positioning a patient in an arms-over-head position for treatment.

BACKGROUND ART

A state of the art device for positioning a patient in an arms-up or arms-over-head position for treatment, is presently made and sold by Smithers Medical Products, Inc., Tallmadge, Ohio, U.S.A. under the trademark Tee-Grip ®. This device is further identified as "Stock No. TG-1" ("Tee-Grip ®" is a registered trademark of Smithers Medical Products, Inc., Tallmadge, Ohio, U.S.A.). This device is a repositioning device which comprises a horizontal rectangular base, a head positioning member mounted on the base near one end, and a handlebar mounted on the base near the other end. The handlebar comprises a vertically upwardly extending stem which is secured to the base and a pair of hand grips which are attached to the stem near an upper end thereof and which extend laterally horizontally from the stem. The entire device, except for mounting screws (to affix the handlebar and the head positioning member to the base) is made of a hard, rigid acrylic plastic.

The device is placed for use on a horizontal supporting surface (e.g., a patient treatment table) so that the base is horizontal. A patient places his or her head on the head holder or head positioning member, raises the arms above the head and grasps the hand grips.

The device is useful generally for any patient treatment requiring an arms-over-head position. This device is especially useful for lateral lung treatments. It can also be used to improve the accuracy of set-ups for esophagus, breast tangents, and any type of chest or abdominal treatment in which the arms must be over the patient's head. This device allows a patient to raise his or her arms above the head in an accurate and consistent manner.

The prior art device does not comfortably fit patients of all sizes. The distance from the head positioning member to the handlebar grips is fixed. A patient of about average height may grasp the hand grips with arms outstretched and straight. However, a patient of significantly shorter than average stature may have to stretch in order to reach the hand grips and may even be unable to reach the grips when the head is properly positioned on the positioning member. The patient of significantly taller than average stature will have arms bent at the elbow when he or she grasps the hand grips with the arms while the head is properly positioned on positioning member. There is some discomfort and perhaps also some loss of precision in positioning the patient when the patient is either significantly taller or significantly shorter than average.

SUMMARY OF THE INVENTION

This invention provides an adjustable device for positioning a patient in an arms-over-head position for treatment. This device can be adjusted in accordance with the height and reach of a patient, so that a patient of virtually any height can reach the hand grips with outstretched arms which are straight and not bent.

The device of this invention comprises:
a base;
means associated with the base for positioning a head of a patient;
a handlebar support member secured at one end to the base and extending in one direction from the base, said support member having means remote from the base for adjustably supporting a handlebar;
a handlebar adjustably supported by the handlebar support member and having a pair of hand grips which are spaced apart; and
means for adjustably positioning the handlebar and for retaining the handlebar in desired position, so that the hand grips may be adjustably positioned in accordance with the size of a patient undergoing treatment.

DESCRIPTION OF THE PREFERRED EMBODIMENT

Figure 1:
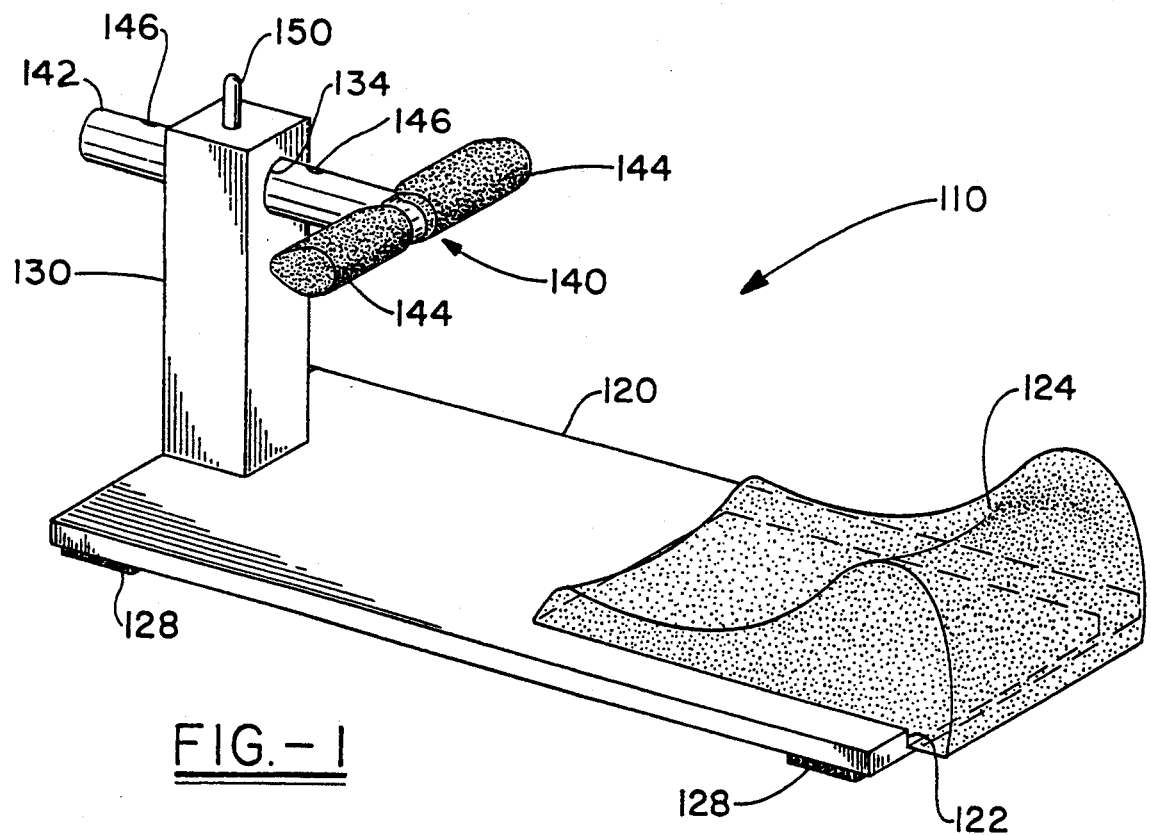
FIG. 1 is a perspective view of a patient positioning device in accordance with this invention.
Figure 2:
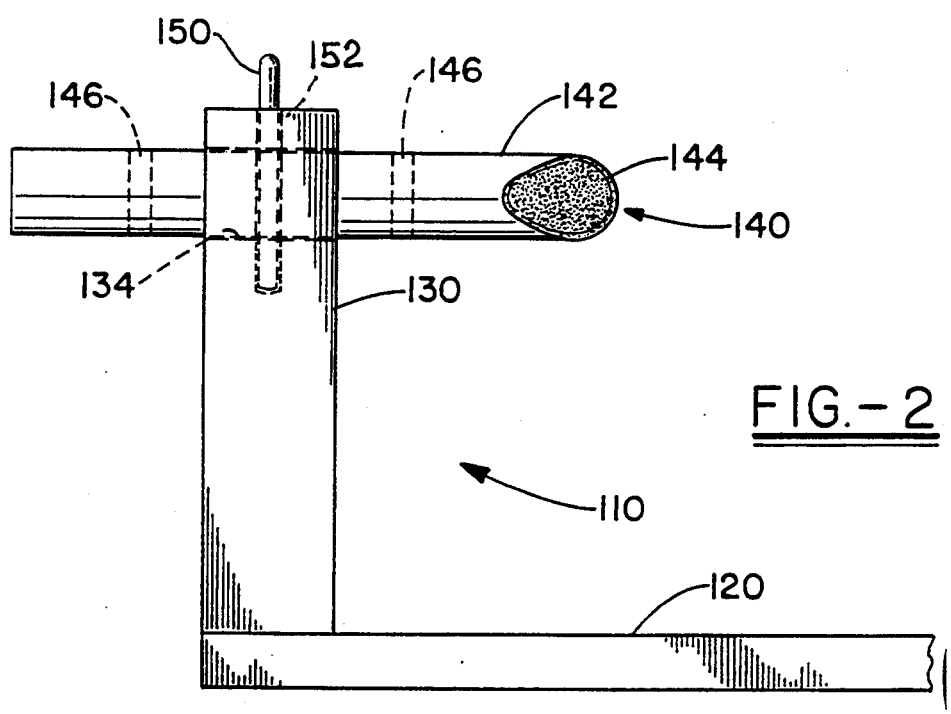
FIG. 2 is a side elevational view of the device shown in FIG. 1.

This invention will now be described in detail with reference to the best mode and preferred embodiment thereof, as illustrated in FIGS. 1 and 2.

Referring now to FIGS. 1 and 2, 110 is a patient grip positioning device in accordance with the preferred embodiment of this invention. Positioning device 110 comprises a base 120 which is adapted to be supported in an essentially horizontal position on an essentially horizontal supporting surface and which has means associated therewith (shown herein as a head-positioning member 124) for accurately and reproducibly positioning a head of a patient; a handlebar support member 130 which is secured at one end to the base 120, which extends in one direction (vertically upwardly) from the base, and which has means remote from said one end for supporting a handlebar; a handlebar 140 which has a pair of hand grips 146 and which is adjustably supported by the handlebar support member 130 so that the hand grips 146 are at a desired distance from a head positioning means or member; and means for adjustably positioning the handlebar in desired position so that the hand grips 146 may be adjustably positioned in accordance with the size of a patient undergoing treatment.

Base 120 is a plate-like rectangular solid having first and second ends and a longitudinal axis extending therebetween. Base 120 also has spaced opposite first and second parallel surfaces (which are an upper surface and lower surface, respectively, when the base is oriented horizontally) and first and second opposite sides.

A cut out 122 for a head positioning member or head rest is provided on the first or upper surface of space 120 near the second end (or foot) of the base 120. This cut out is rectangular in shape and extends longitudinally along the longitudinal axis of the base. The length of this cut out is approximately ⅓ to ½ the total length of the base. This cut out may be in the shape of a rectangular prism.

A head-positioning member 124, shown in FIG. 3, is received in cut out 122 for the purpose of supporting and accurately positioning a head of a patient undergoing treatment. This head-positioning member extends upwardly from the first or upper surface of base 120.

Four feet 128, one at each corner of base 120 on the underside or second surface thereof, are provided near each of the corners of base 120 for supporting the same on a horizontal surface, such as a floor or a patient examination table.

Base 120 and indeed the entire device 110 except for screws and pins, is made of a rigid transparent acrylic plastic or polymer, or other desired strong, hard, rigid plastic or polymeric material. The feet 128 on the other hand, are preferably made of a material having some degree of resiliency, e.g., an elastomeric material such as rubber so that they will grip a surface on which the device 110 is placed without damaging the finish of such surface.

A pair of holes (not shown) are provided in side-by-side relationship on opposite sides of the longitudinal axis near the first or head end of base 120, for the purpose of receiving an upright handlebar support member or handlebar base 130.

Handlebar support member or handlebar base 130 is secured to base 120 and extends in one direction, i.e., upwardly, from base 120. Thus, handlebar support member 130 is upright and preferably vertical when the device 110 is in its normal orientation for use, with base 120 horizontal. Handlebar support member 130 is also preferably made of a hard transparent acrylic polymer. Handlebar support member 130 is preferably of rectangular cross-section as shown, although this is by no means critical.

Handlebar support member 130 has opposite first (or lower) and second (or upper) ends. The first or lower end may be received in a hole or socket in the base. This hole or socket has the same cross-sectional shape as that of the handlebar support member 130. The hole or socket in the base and the lower end of the handlebar support member 130 may together form a conventional joint, such as a dowel joint or preferably, a mortise and tenon joint. A pair of screws (not shown) secure the first end of the handlebar support member 130 to the base 120. These screws are preferably made of an acrylicepoxy plastic (which is strong and hard and will not rust) although metallic screws can be used instead if desired.

The head-positioning member 124 and the handlebar support member 130 are in spaced apart relationship. The handlebar support member 130 is mounted on the base 120 near the first or head end thereof, and the headpositioning device 124 is mounted on the base near the second end or foot thereof.

Handlebar support member 130 has a hole 134 extending longitudinally therethrough near the second or upper end, for receipt of a handlebar 140.

Handlebar 140 comprises a cylindrical stem or shaft 142 of preferably circular cross-section (although polygonal shapes such as square and hexagonal shapes are also acceptable) and a pair of laterally-extending spaced apart hand grips 144 affixed to stem 142 on opposite sides of stem 142 at one end thereof. The cross-sectional shape of the handlebar stem 142 and the hole 134 in the handlebar support member 130 are the same.

The handlebar 140 is capable of adjustable positioning in the handlebar support member 130, so that the distance from the hand grip 144 to the head positioning member 124 may be either greater or less, to accommodate the needs of patients having different heights and consequently different arm lengths. To this end, the stem 142 of handlebar 140 may be inserted in either direction in hole 134. As shown in the drawings, the handlebar stem 142 is inserted in inboard fashion so that the hand grips 144 are above the base 120. This meets the needs of a patient of short to medium height. Alternatively, for a taller patient, the handlebar stem may be inserted in the opposite direction so that the hand grips lie outboard of the base (i.e., beyond the perimeter or first end of base 120). This fits the needs of a taller patient. As a further aid in adjustably mounting or positioning the handlebar 140 in the handlebar support member 130, the stem 142 of the handlebar 140 is slidable in hole 134 (to place the grips 144 closer to or farther from the head positioning member 124) and has a plurality (preferably three as in the preferred embodiment) of spaced apart holes 146 extending transversely therethrough, to receive a fastening pin 150. Fastening pin 150 extends vertically down from the top or second end of handlebar support member 130 through a centrally located vertical hole 152 in the handlebar support member and through a selected one of the holes 146 in the handlebar stem 142. (The user aligns a desired hole 146 with hole 152). This permits the user of the device 110 to select any one of six positions for the handle 140 (three positions when the handle bar is in the inboard orientation shown in the drawings and three more positions when the handle bar 140 is in an outboard position) and to secure the handlebar 140 in place in desired position, simply by inserting the pin 150 through a selected one of the holes 146 in shaft 142.

The adjustable mounting or positioning of the handlebar 140 in the supporting member 130 enables a user of the device 110, say a medical technician, to position the hand grips 144 either closer to or farther from the head positioning member 124 in accordance with the arm length of the patient. The hand grips 144 should be so positioned so that the patient has to reach his or her arms extended straight (i.e., not bent at the elbow) and extended over the head in order to grasp the hand grips 144. On the other hand, the distance from the hand grips 144 to the head positioning member 124 should not exceed the length of the patient's arms, and the device of this invention makes that possible also. The device of this invention provides a wide range of adjustability to accommodate the needs of patient's needs of widely varying heights.

The device of the present invention makes it possible to position a patient precisely, and on subsequent visits to reposition the patient in precisely the same position as the position as assumed during the first visit. This is very beneficial for photographic imaging, e.g., x-ray and MRI (magnetic resonance imaging), when a series of photographs are to be taken over time. Since the patient is positioned in exactly the same way during each visit, so that the images obtained in each visit are taken in exactly the same location (e.g., the same plane in the human body) so that a series of images obtained over time during this series of patient visits will be directly comparable.

The device of this invention, is useful generally for medical diagnosis, imaging and its treatment wherein the patient assumes a position with the arms above the head. Thus, the device of this invention can be used for lateral lung treatments, and to improve the accuracy of setups for esophagus, breast tangents, and any type of chest or abdominal treatment where the arms must be over the patient's head.

In operation, the positioning device 110 is placed on a flat horizontal surface, such as a floor or a patient treatment table, so that the base 120 is horizontal (or at least essentially horizontal) or level. The handlebar support member 130 then extends vertically upwardly, and the hand grips 144 are supported at an elevation higher than that of the base 120 and the supporting surface. A patient then lies down on the supporting surface with the head supported on head positioning member 124. The patient then extends his or her arms up over his or her and grasps the hand grips 144. The user or operator, usually a medical professional such as a medical technologist or technician, then adjusts the portion of the handlebar 140 and its hand grips 144 in the manner described above, i.e., by inserting the handlebar stem 142 in hole 134 in one direction or the other, depending on the height and arm length of the patient and then sliding the stem 142 in the hole 134 until the patient's arms are straight. The operator then locks the handlebar 140 in position by aligning the nearest hole 146 in stem 142 with the vertical pin-receiving bore 152 at the upper end of handlebar support member 130 and inserting fastening pin 150.

By way of illustration, the dimensions shown in Table 1 below have been found to represent preferred dimensions for the preferred embodiment of device 110 as shown in the drawings. All dimensions given in inches, with corresponding dimensions in centimeters shown in parentheses. It will be understood that these dimensions may be varied as desired.

TABLE I

| Base 120: | |
|---|---|
| Length, inches (cm) | 20 (50.8) |
| Width, inches (cm) | 10 (25.4) |
| Thickness (depth), inches (cm) | |
| Cutout 122: | 0.75 (1.9) |
| Depth, inches (cm) | 0.375 (0.95) |
| Handlebar Support Member 130: | |
| Height, inches (cm) | 8 (20.3) |
| Width, inches (cm) | 3 (7.6) |
| Depth, inches (cm) | 2 (5.1) |
| Distance from nearest edge of base, inches (cm) | 0.5 (1.27) |

As will be apparent to those skilled in the art, various modifications can be made without departing from the scope and spirit of this invention. For example, the base of the device may be square, elliptical (or oval) or circular, instead of rectangular as shown. Each of these shapes has a longitudinal axis and a transverse axis. The transverse axis may be either shorter than or equal in length to the longitudinal axis. Where the longitudinal and transverse axes of equal length (e.g., in the case of a circular or a square base), the longitudinal axis is the axis on which both the head-positioning element 124 and the handlebar supporting element 130 are placed in spaced-apart relationship.

The handlebar may have configurations other than that shown in the drawings. For example, instead of the T-shaped handlebar 140 comprising a longitudinal stem 142 and transverse grips 144 as shown, the handlebar may comprise a single curved and transversely extending bar, which may be either generally U-shaped or in the shape of a double-S curve (i.e., a shape resembling the horns of a longhorn steer), in the hand grips at each end of the bar. Both of these shapes are known handlebar shapes. Either of these shapes requires a transverse hole in place of the longitudinal hole 134 in the upright handlebar support member 130. Also, the distance from the hand grips to the head-positioning member 124 would be varied by rotating the bar and then locking the bar in place after it is rotated to the desired position.

Instead of mounting handlebar 140 in a hole 134 in the handlebar support member 130, one may adjustably mount a handlebar 140 on handlebar support member 130 by means of a mounting bracket affixed to the handlebar support member. This mounting bracket may have a C-shaped clamp which encircles a substantial portion of the perimeter or circumference of the handlebar stem or shaft 142.

The above modifications are merely illustrative. Other modifications will occur to those skilled in the art.

While this invention has been described in detail with reference to specific embodiments and with particular reference to the preferred embodiment, this description is by way of illustration and not limitation as will be apparent to those skilled in the art, various modifications can be made without departing from the scope and spirit of this invention.

What is claimed is:

1. A device for positioning a patient in an arms-overhead position for treatment, said device comprising:
    (a) a base;
    (b) head positioning means associated with said base for positioning a head of a patient;
    (c) a handlebar support member extending in one direction of said base, said support member having a first end which is secured to said base and a second end which is remote from said base, said support member having means remote from said first end for adjustably supporting a handlebar;
    (d) a handlebar adjustably supported by said support member, said handlebar comprising a longitudinally extending stem which is slidable relative to said handlebar support member, and a pair of hand grips which are affixed to said stem at one end thereof and extend laterally in opposite directions from said stem; and
    (e) means for adjustably positioning said handlebar and for retaining said handlebar in desired position, whereby the hand grips may be adjustably positioned in accordance with the size of a patient undergoing treatment.

2. A device according to claim 1, wherein said base has a longitudinal axis, wherein further said handlebar support member is secured to said head base at a first location along said longitudinal axis, and wherein further said positioning means is at a second location along said longitudinal axis which is spaced from the first location.

3. A device according to claim 2, wherein said base is rectangular.

4. A device according to claim 3, wherein said base has first and second ends and wherein further said handlebar support member is secured to said base near the first end thereof and said head positioning means is mounted on said base near the second end thereof.

5. A device according to claim 4, wherein said base is adapted to be supportd in a horizontal position and said handlebar support member extends upwardly from said base.

6. A device according to claim 1 wherein said handlebar is slidable in a hole in said handlebar support member.

7. A device according to claim 6 wherein said stem has a plurality of spaced apart holes extending transversely therethrough to receive a fastening pin.

* * * * *